(12) United States Patent
Birnkrant

(10) Patent No.: US 12,379,308 B2
(45) Date of Patent: Aug. 5, 2025

(54) ENVIRONMENTAL ENCLOSURE FOR A TRANSPORT GAS SENSOR

(71) Applicant: Carrier Corporation, Palm Beach Gardens, FL (US)

(72) Inventor: Michael J. Birnkrant, Wethersfield, CT (US)

(73) Assignee: CARRIER CORPORATION, Palm Beach Gardens, FL (US)

( * ) Notice: Subject to any disclaimer, the term of this patent is extended or adjusted under 35 U.S.C. 154(b) by 52 days.

(21) Appl. No.: 17/949,850

(22) Filed: Sep. 21, 2022

(65) Prior Publication Data

US 2023/0097844 A1 Mar. 30, 2023

Related U.S. Application Data

(60) Provisional application No. 63/250,636, filed on Sep. 30, 2021.

(51) Int. Cl.
| | |
|---|---|
| *G01N 21/25* | (2006.01) |
| *F24F 11/36* | (2018.01) |
| *F24F 11/89* | (2018.01) |
| *G01N 21/3504* | (2014.01) |

(52) U.S. Cl.
CPC ............ *G01N 21/255* (2013.01); *F24F 11/36* (2018.01); *F24F 11/89* (2018.01); *G01N 21/3504* (2013.01); *G01N 2201/022* (2013.01)

(58) Field of Classification Search
CPC ............ G01N 21/3504; G01N 21/255; G01N 2201/022; G01N 21/359; F24F 11/36; G01J 5/045
See application file for complete search history.

(56) References Cited

U.S. PATENT DOCUMENTS

| | | | |
|---|---|---|---|
| 7,069,768 | B2 | 7/2006 | Weckstrom et al. |
| 7,541,587 | B2 | 6/2009 | Cutler et al. |
| 9,804,084 | B2 | 10/2017 | Kouznetsov et al. |
| 2012/0235038 | A1 | 9/2012 | Nishikawa et al. |
| 2019/0257782 | A1 | 8/2019 | Yang et al. |
| 2020/0116632 | A1* | 4/2020 | Henderson ............. G01N 21/15 |

(Continued)

FOREIGN PATENT DOCUMENTS

| | | |
|---|---|---|
| CN | 104280358 A | 1/2015 |
| CN | 204086116 U | 1/2015 |

(Continued)

OTHER PUBLICATIONS

CN111721735A Translation (Year: 2020).*

(Continued)

*Primary Examiner* — Schyler S Sanks
(74) *Attorney, Agent, or Firm* — CANTOR COLBURN LLP

(57) ABSTRACT

A refrigerant detection assembly operable to detect refrigerant mixed with air includes a housing having an internal cavity fluidly connected with an ambient atmosphere surrounding the housing via at least one opening and a sensor subassembly mounted within the internal cavity. The sensor subassembly includes a sensor, a printed circuit board, a heat preservation housing mechanically and thermally coupled to the printed circuit board, and at least one shielding component mechanically coupled to the printed circuit board.

18 Claims, 4 Drawing Sheets

(56) References Cited

U.S. PATENT DOCUMENTS

| | | | |
|---|---|---|---|
| 2020/0124564 A1 | 4/2020 | Xiao et al. | |
| 2020/0271343 A1* | 8/2020 | Crawford | F24F 3/001 |
| 2020/0386431 A1 | 12/2020 | Kondrk et al. | |
| 2020/0393140 A1 | 12/2020 | Nouchi | |
| 2021/0108820 A1 | 4/2021 | Hovardas et al. | |
| 2021/0156795 A1 | 5/2021 | Wan et al. | |

FOREIGN PATENT DOCUMENTS

| | | | |
|---|---|---|---|
| CN | 205262956 U | | 5/2016 |
| CN | 206339487 U | | 7/2017 |
| CN | 107328730 A | | 11/2017 |
| CN | 304583115 | | 4/2018 |
| CN | 109507140 B | | 10/2018 |
| CN | 109507140 | | 3/2019 |
| CN | 208636208 U | | 3/2019 |
| CN | 209069825 U | | 7/2019 |
| CN | 110132877 A | | 8/2019 |
| CN | 110907385 A | | 3/2020 |
| CN | 111721735 A | * | 9/2020 |
| CN | 112099421 A | | 12/2020 |
| CN | 212228731 U | | 12/2020 |
| CN | 113007863 A | | 6/2021 |
| CN | 213937742 U | | 8/2021 |
| DE | 102015115047 A1 | | 3/2017 |
| EP | 2373978 B1 | | 3/2016 |
| WO | 2021041359 A1 | | 3/2021 |

OTHER PUBLICATIONS

"AM4205 NDIR A2L Refrigerant/Gasoline Sensor"; Specification; Version V0.1; Date: Jan. 20, 2021; www.gassensor.com.cn; 10 pages.

"Molecular Property Spectrometer (MPS) A2L Refrigerant Gas Sensor User Manual"; Nevada Nanotech Systems Inc.; NNTS Proprietary Information; 2020; 23 pages.

"NDIR gas sensor A2L"; Subic Sensor and Instrument Co., Ltd.; www.gassensor.com.cn; 1 page.

"New A2L refrigerant sensor technology comes to Europe"; Cooling Post; Oct. 3, 2020; 3 pages.

* cited by examiner

ENVIRONMENTAL ENCLOSURE FOR A TRANSPORT GAS SENSOR

CROSS-REFERENCE TO RELATED APPLICATIONS

This application claims the benefit of U.S. Provisional Application No. 63/250,636 filed Sep. 30, 2021, the disclosure of which is incorporated herein by reference in its entirety.

BACKGROUND

Exemplary embodiments of the present disclosure relate to refrigeration systems, and more particularly, to a detection assembly and a refrigeration system incorporating the detection assembly for detecting leaks of moderate to low global warming potential (GWP) refrigerants.

Refrigeration systems, as used in HVAC applications, utilize refrigerant within a closed loop circuit to condition air provided to an area or enclosed space. This refrigerant, historically, has been provided as a fluid with a high global warming potential (GWP) value such as R134A or R410A. Thus, although the refrigerants that have been used previously are effective coolants, the negative effect they can have on the environment has led to regulatory requirements to transition to refrigerants which have moderate-to-low GWP values.

Modern refrigerants, for example A2L refrigerants, comply with environmental regulations relating to global warming potential (GWP). In order to comply with the proposed GWP regulations, hydrofluorocarbon (HFC) and hydrocarbon refrigerants with various levels of flammability are being developed and are being considered for use in HVAC systems.

As with any system, there is a potential for flammable refrigerants used in HVAC applications to leak and migrate to undesirable areas in the vicinity of the HVAC system that may contain an ignition source. When the flammable refrigerants, in the presence of air or another oxidizer, are exposed to an ignition source, the potential for a combustion event exists.

BRIEF DESCRIPTION

According to an embodiment, a refrigerant detection assembly operable to detect refrigerant mixed with air includes a housing having an internal cavity fluidly connected with an ambient atmosphere surrounding the housing via at least one opening and a sensor subassembly mounted within the internal cavity. The sensor subassembly includes a sensor, a printed circuit board, a heat preservation housing mechanically and thermally coupled to the printed circuit board, and at least one shielding component mechanically coupled to the printed circuit board.

In addition to one or more of the features described above, or as an alternative to any of the foregoing embodiments the sensor is a non-dispersive infrared sensor.

In addition to one or more of the features described above, or as an alternative to any of the foregoing embodiments the non-dispersive infrared sensor includes a light source and a detector element, the light source and the detector element being mounted to the printed circuit board.

In addition to one or more of the features described above, or as an alternative to any of the foregoing embodiments the at least one shielding component further comprises a top shielding component and a bottom shielding component, the top shielding component being mechanically fastened to the bottom shielding component.

In addition to one or more of the features described above, or as an alternative to any of the foregoing embodiments the top shielding element is arranged upwardly adjacent the heat preservation housing and the bottom shielding component is positioned adjacent a bottom surface of the printed circuit board.

In addition to one or more of the features described above, or as an alternative to any of the foregoing embodiments the sensor is encased between the heat preservation housing and the printed circuit board.

In addition to one or more of the features described above, or as an alternative to any of the foregoing embodiments the heat preservation housing has at least one hole formed therein.

In addition to one or more of the features described above, or as an alternative to any of the foregoing embodiments the subassembly further comprises at least one active heating element operably coupled to the non-dispersive infrared sensor.

In addition to one or more of the features described above, or as an alternative to any of the foregoing embodiments comprising a film disposed in overlapping arrangement with the at least one opening, wherein the film is permeable to gas and impermeable to liquid.

According to an embodiment, a heating ventilation and air conditioning (HVAC) system includes a heat exchanger arranged within a closed loop refrigerant circuit and a refrigerant detection assembly operable to detect refrigerant from the closed loop refrigerant circuit mixed with air. The refrigerant detection assembly includes a housing having an internal cavity and an opening such that a flow path extends from the opening into the internal cavity and a sensor subassembly mounted within the internal cavity. The sensor subassembly includes a sensor, a printed circuit board, a heat preservation housing mechanically and thermally coupled to the printed circuit board, and at least one shielding component mechanically coupled to the printed circuit board.

In addition to one or more of the features described above, or as an alternative to any of the foregoing embodiments the heat exchanger is an evaporator and the refrigerant detection assembly is mounted adjacent to the evaporator coil.

In addition to one or more of the features described above, or as an alternative to any of the foregoing embodiments the refrigerant detection assembly is operable to detect a leak within the closed loop refrigerant circuit within ten seconds of being exposed to 100% of a lower flammability limit.

In addition to one or more of the features described above, or as an alternative to any of the foregoing embodiments the refrigerant detection assembly detects a leak within the closed loop refrigerant circuit when the refrigerant measured by the non-dispersive infrared sensor is at least 25% of a lower flammability limit.

In addition to one or more of the features described above, or as an alternative to any of the foregoing embodiments the sensor integrated with the printed circuit board.

In addition to one or more of the features described above, or as an alternative to any of the foregoing embodiments the sensor is a non-dispersive infrared sensor.

In addition to one or more of the features described above, or as an alternative to any of the foregoing embodiments the sensor subassembly further comprises at least one active heating element operably coupled to the sensor.

In addition to one or more of the features described above, or as an alternative to any of the foregoing embodiments the at least one shielding component further comprises a top shielding component and a bottom shielding component, the top shielding component being mechanically fastened to the bottom shielding component.

In addition to one or more of the features described above, or as an alternative to any of the foregoing embodiments comprising a film disposed in overlapping arrangement with the opening, the film being permeable to gas and impermeable to liquid.

BRIEF DESCRIPTION OF THE DRAWINGS

The following descriptions should not be considered limiting in any way. With reference to the accompanying drawings, like elements are numbered alike.

DETAILED DESCRIPTION

A detailed description of one or more embodiments of the disclosed apparatus and method are presented herein by way of exemplification and not limitation with reference to the Figures.

Figure 1:
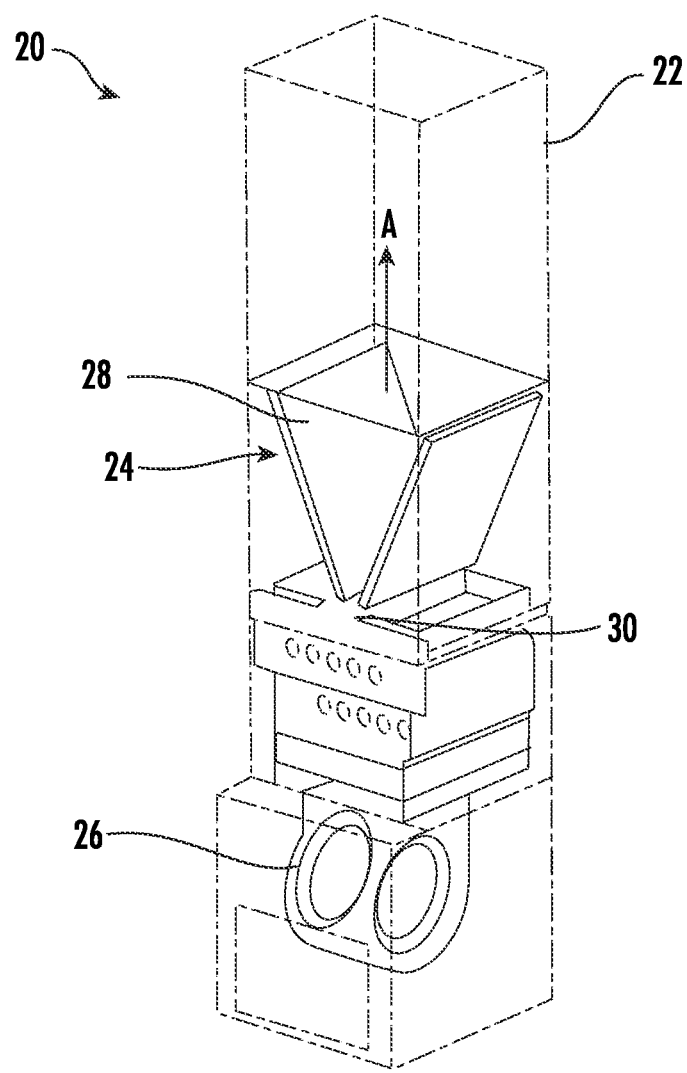
FIG. 1 is a schematic diagram of an exemplary HVAC system, depicted as a furnace coil or fan coil unit, according to an embodiment.

With reference now to FIG. 1, an example of a heating, ventilation, and air conditioning (HVAC) system 20 is illustrated, depicted as a furnace coil or fan coil unit 20. Although described herein as furnace or fan coil unit it should be appreciated that the HVAC system 20 may be any beating or cooling system. As shown, the furnace coil or fan coil unit 20 includes a cabinet or housing duct 22 within which various components of the HVAC system are located. For example, housed within the cabinet 22 of the furnace coil or fan coil unit 20 is a heat exchanger assembly 24 configured to heat and/or cool the adjacent air. A blower or fan assembly 26 may also be arranged within the cabinet 22 or alternatively, at a position outside of but in fluid communication with the cabinet 22. The blower 26 is operable to circulate a flow of air A through the interior of the cabinet 22, across the heat exchanger assembly 24. Depending on the desired characteristics of the furnace coil or fan coil unit 20, the blower 26 may be positioned either downstream with respect to the heat exchanger assembly 24 (i.e., a "draw through" configuration), or upstream with respect to the heat exchanger assembly 24 (i.e., a "blow through" configuration), as shown in FIG. 1.

The heat exchanger assembly 24 is part of a closed loop refrigeration circuit and may include any of a plurality of configurations. As illustrated in FIG. 1, the heat exchanger assembly 24 includes one or more heat exchanger coils 28 arranged in a non-linear configuration. For example, the heat exchanger assembly 24 may have a generally V-shaped configuration, a generally A-shaped configuration, or a generally N-shaped configuration, as is known in the art. In other embodiments, the heat exchanger assembly 24 may include a single heat exchanger coil 28 arranged at an angle with respect to the flow path of air A through the cabinet 22. In embodiments where the furnace coil or fan coil unit 20 is configured to provide cool air, the heat exchanger assembly 24 functions as an evaporator. The refrigerant circulating through the heat exchanger assembly 24 absorbs heat from the air A passing through the heat exchanger assembly 24 and the resultant cool air A is provided to a space to be conditioned.

In an embodiment, the refrigerant circulating through the HVAC system 20 is an A2L refrigerant. The classification of refrigerant is based upon American Society of Heating, Refrigerating and Air-Conditioning (ASHRAE) Standard 34. The standard evaluates each refrigerant's flammability and toxicity and gives it a class referenced as a letter and number combination. The first letter refers to the refrigerants' toxicity and is based on the particular refrigerant's occupational exposure limit (OEL). The number adjacent to the letter refers to the refrigerants' flammability and is based on the burning velocity (BV), heat of combustion (HOC), and lower flammability limits (LFL) of the particular refrigerant.

With continued reference to FIG. 1, in rare instances the refrigerant within the closed loop refrigerant circuit of the HVAC system 20 may leak. When A2L refrigerants are used in the HVAC system 20 a leak of refrigerant could lead to undesirable consequences due to the mildly flammable nature of A2L refrigerants. Accordingly, in an embodiment, the HVAC system 20 includes at least one refrigerant detection assembly 30 operable to detect a refrigerant leak therein. For example, at least one refrigerant detection assembly 30 may be located near the heat exchanger assembly 24. In an embodiment, the at least one refrigerant detection assembly 30 is adjacent to at least one coil 28 of the heat exchanger assembly 24. to detect gaseous refrigerant located external to the at least one tube of the heat exchanger coil 28. However, embodiments where a refrigerant detection assembly 30 is alternatively or additionally arranged at any suitable location relative to the refrigeration system 20 to detect a leak therein is also within the scope of the disclosure. In an embodiment, the refrigerant detection assembly 30 enables the detection of leaks within ten seconds of being exposed to 100% lower flammability limit (LFL). In another embodiment, the refrigerant detection assembly 30 enables the detection of leaks within thirty seconds of being exposed to 25% lower flammability limit (LFL). A lower flammability limit (LFL) of a refrigerant is the minimum concentration limit that is required for the refrigerant to become potentially combustible. It is envisioned that the refrigerant detection assembly 30 described herein may be capable of detecting a leak of at least one A2L refrigerant when the refrigerant detection assembly 30 detects at least 5 to 50% LFL in the sample.

Figure 2:
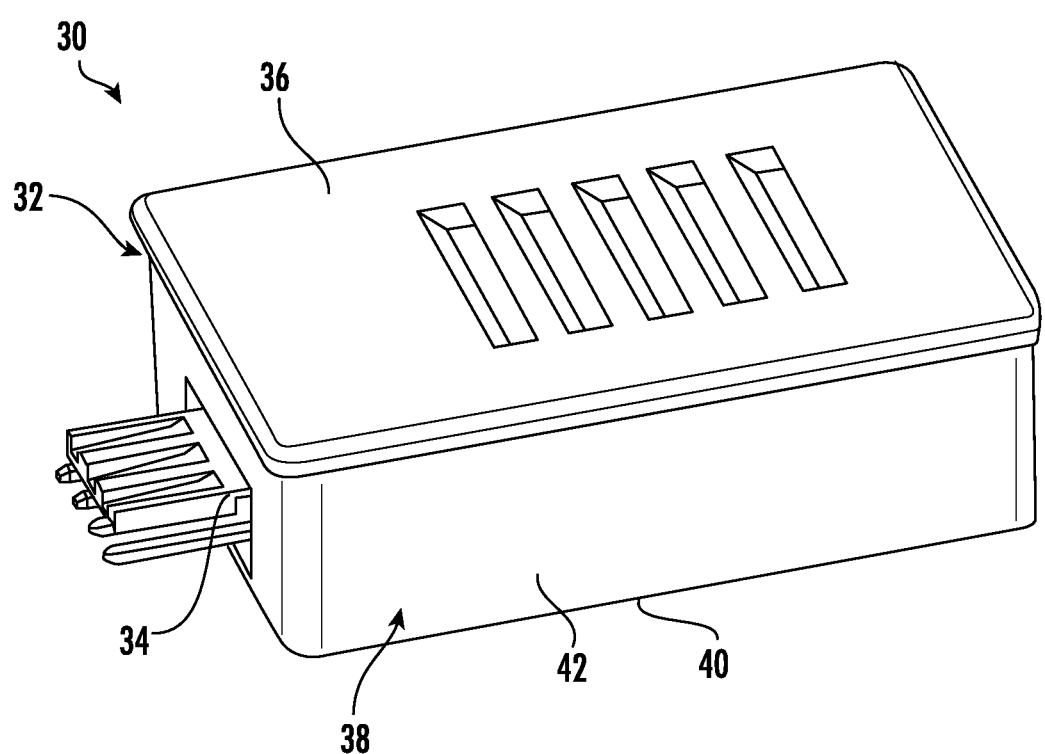
FIG. 2 is a schematic diagram of an exemplary environmental enclosure for an HVAC system refrigerant detection assembly according to an embodiment.
Figure 3:
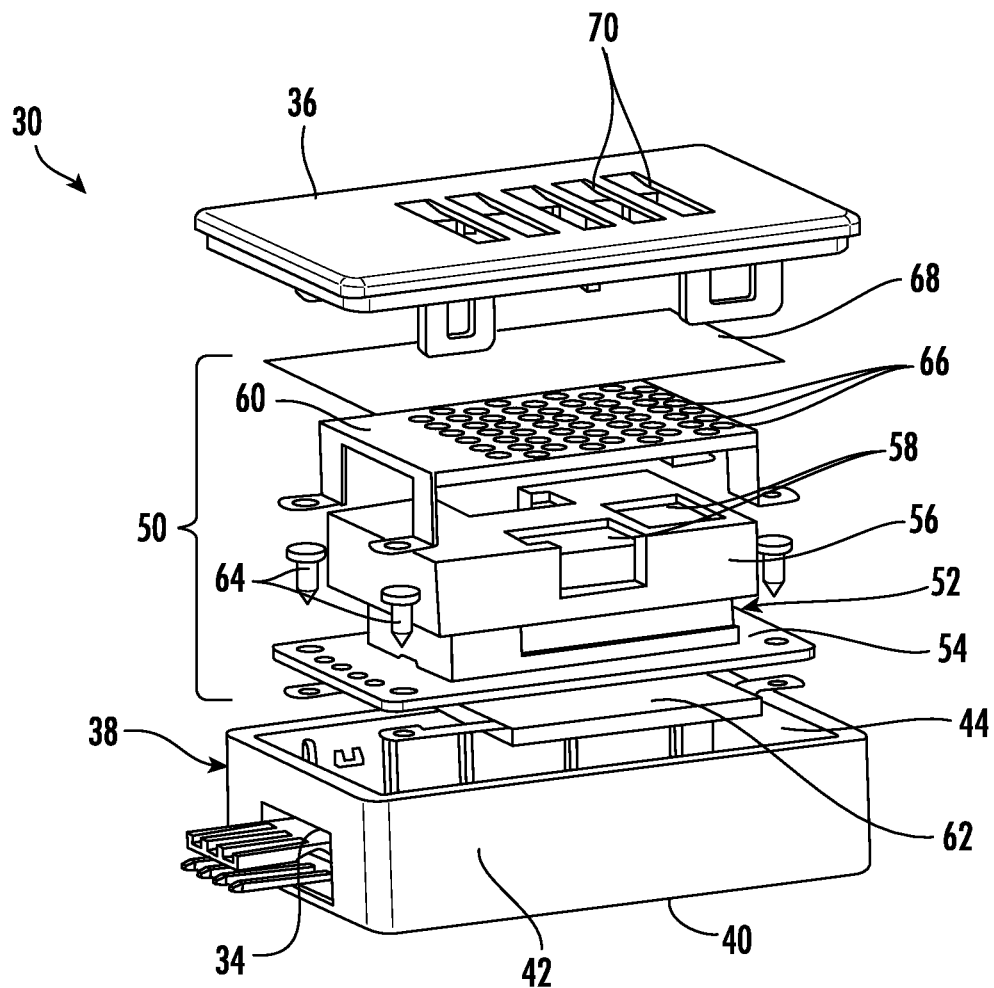
FIG. 3 is an exploded perspective view of a refrigeration detection assembly according to an embodiment.
Figure 4:
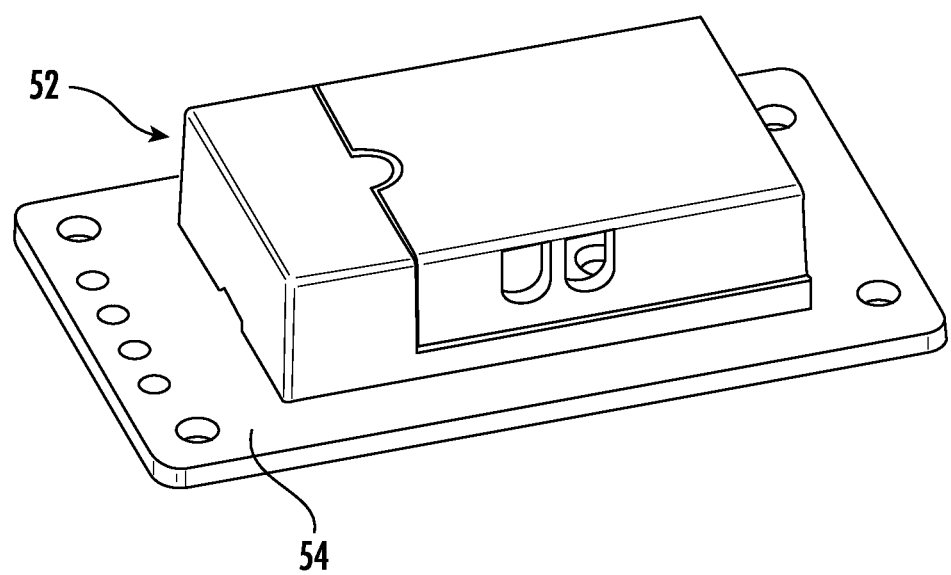
FIG. 4 is a perspective view of an exemplary portion of the refrigeration detection assembly of FIG. 3 according to an embodiment.

An environmental enclosure for a refrigerant detection assembly 30 increases robustness, reliability and performance of the refrigerant detection assembly 30 during operation of the system. An example of a refrigerant detection assembly 30 having such an environmental enclosure is illustrated in more detail in FIGS. 2-4. The refrigerant detection assembly 30 includes a housing 32. In an embodiment, the refrigerant detection assembly 30 is configured to mechanically or chemically integrate or couple to a component of the HVAC system 20, such as using one or more mounting holes (not shown) formed in the housing 32 or an adhesive for example. Further, the refrigerant detection assembly 30 may be configured to electrically integrate with the HVAC system 20 via one or more connectors 34 formed in the housing 32. In an embodiment, connector 34 may be configured to prevent incorrect electrical integration with the HVAC system 20. For example, the connector 34 may include a plastic protrusion that is shaped to match the electrical wire harness used for integration.

In the illustrated, non-limiting embodiment, the housing 32 is formed from a separate cover 36 and base 38 that are generally complementary in size and shape. The cover 36 and base 38 may be formed from a durable material, such as plastic or resin for example. The cover 36 may be removably coupled to the base 38, such as via a plurality of fasteners or a snap fit connection, or alternatively, may be permanently affixed thereto. In an embodiment, the base 38 has a bottom 40 and a plurality of sidewalls 42 extending from the bottom 40 such that an internal cavity 44 is defined between the bottom 40 and the plurality of sidewalls 42. Accordingly, the cover 36 may be configured to couple to or seat against the distal end of the plurality of sidewalls 42 to seal the cavity 44. However, it should be understood that embodiments where the cavity 44 is alternatively formed in the cover 36 and embodiments where the cavity 44 is defined by the cover 36 and the base 38 in combination are also contemplated herein.

A sensor subassembly 50 is positionable within the cavity 44 of the housing 32. The sensor subassembly includes a sensor 52. In an embodiment, the sensor 52 is a non-dispersive infrared (NDIR) sensor including an infra-red light source (not shown) and at least one corresponding detector element (not shown). As is known in the art, a NDIR sensor is configured to use light, for example infrared light, to evaluate the absorption characteristics of gas molecules within the light path. The gas molecules are identified and the concentration of the gas molecules may be determined by utilizing the relation (Lambert-Beer law) between the gas concentration and the absorption intensity. The NDIR sensor is configured to detect the presence of refrigerant molecules, such as an A2L refrigerant for example. Accordingly, when a leak is present, the sample at the sensor 52 will contain a mixture of air and refrigerant.

A printed circuit board 54 is disposed generally adjacent to a portion, such as the bottom surface for example, of the sensor 52. In an embodiment, the printed circuit board 54 includes the circuitry and/or other components associated with operation of the sensor 52, such as the light source and detector element for example. Accordingly, the printed circuit board 54 and the sensor 52 in combination may be considered to form a sensor core. The printed circuit board 54 may include signal amplification and conditioning electronics.

The printed circuit board 54 may be directly connected to a power source, or alternatively, may be adapted to receive one or more batteries sufficient to provide power thereto to operate the refrigerant detection assembly 30 for an extended period of time. In such embodiments, the power provided by the batteries may be the sole source of power used to operate the refrigerant detection assembly 30 or alternatively, may be supplemental to the power source, for example in the event of a failure or loss of power at the power source. The printed circuit board 54 is configured to form an interface between the sensor 52 and the connectors to provide power and data to or from the HVAC system 20.

In an embodiment, the heat generated by the infra-red light source and/or the other electrical components associated with or powered by the printed circuit board 54 may be sufficient to maintain the sensor 52 at a temperature above ambient to prevent condensation and/or frosting. However, in other embodiments, the printed circuit board 54 may include one or more resistive heaters, also referred to herein as active heating elements, embedded therein. In an embodiment, the sensor subassembly 50 includes a heat preservation housing 56 mounted about the sensor 52. The heat preservation housing 56 may be formed from any suitable material, including but not limited to a rigid foam for example. In the illustrated, non-limiting embodiment, the heat preservation housing 56 is configured to abut an upper surface of the printed circuit board 54 such that the sensor 52 is encased between the heat preservation housing 56 and the printed circuit board 54. As shown, the heat preservation 56 has one or more openings 58 formed in an upper surface thereof to form entry and exit locations for a flow of air being sampled by the sensor 52. In an embodiment, the heat preservation housing 56 reduces the gas transport path and increases the robustness of the sensor 52 to frost and condensing conditions by insulating the sensor 52.

The sensor subassembly 50 may further include at least one shielding element configured not only to provide structural support and/or stabilization for the sensor 52, but also to isolate the sensor 52 from vibration, electrical noise, and other emissions within the environment of the HVAC system 20. The at least one shielding element may further prevent the accumulation of frost or condensation on the sensor 52. In an embodiment, the at least one shielding element includes a top shielding element 60 positioned in overlapping arrangement with the heat preservation housing 56 and a bottom shielding element 62 positioned adjacent to a bottom surface of the printed circuit board 54, opposite the sensor 52. The top shielding element 60 provides increases the resistance of the sensor 52 to electromagnetic interference and the bottom shielding element provides electromagnetic shielding for the sensor 52, inhibits water pooling on the electronics, and dissipates heat to reduce the overall size of the sensor 52.

Furthermore, in embodiments including a plurality of shielding elements, such as the top and bottom shielding elements 60, 62 for example, the plurality of shielding elements 60, 62 may be affixed to one another to provide enhanced structural rigidity. For example, in the illustrated, non-limiting embodiment, a plurality of fasteners 64 extend through the printed circuit board 54 to connect the top and bottom shielding elements 60, 62. In embodiments where the sensor subassembly 50 includes at least one shielding element, such as top shielding element 60, positioned above an upper surface of the sensor 52, the top shielding element 60 has a plurality of openings 66 formed therein.

A portion of the housing 32, such as the cover 36 for example, has one or more openings 70 formed therein to define a flow path between the ambient atmosphere surrounding the refrigerant detection assembly 30 and the sensor 52. In operation, air is provided to the interior cavity 44 of the housing 32 via the openings 70. In an embodiment, a breathable film 68, selectively permeable to certain elements, may be mounted within the cavity 44 at a position above the sensor 52. In an embodiment, the breathable film 68 is in direct contact with and overlaps the upper surface of the top shielding element 60. Accordingly, the top shielding element 60 provides mechanical support for the breathable film. By positioning the breathable film 68 over the openings 66 in the top shielding element 60, gasses that enter the housing 32 via the openings 70 are able to permeate through the breathable film 68, through the openings 66 in the shielding component 60, and through the openings 58 formed in the heat preservation housing 56 to reach the sensor 52. However, contaminants such as dust, oil droplets and moisture in the form of liquid are prevented from entering the sensor 52 and from damaging the printed circuit board 54.

The refrigerant detection assembly 30 components are combined to enable environmental robustness. The components may be selected and oriented to reduce the impact of moisture on operation of the sensor 52 or detection of refrigerant by limiting water intrusion and reducing condensation buildup and removing condensation when present. Furthermore, the components may be integrated to enable mechanical robustness while allowing fluid connection with the refrigeration unit 30. The flow path defined by openings 70, breathable film 68, and openings 66 and 58 connecting the ambient environment to the sensor 52 may also be selected to reduce the time for a gas to reach the sensor 52 for sampling.

The term "about" is intended to include the degree of error associated with measurement of the particular quantity based upon the equipment available at the time of filing the application.

The terminology used herein is for the purpose of describing particular embodiments only and is not intended to be limiting of the present disclosure. As used herein, the singular forms "a", "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, element components, and/or groups thereof.

While the present disclosure has been described with reference to an exemplary embodiment or embodiments, it will be understood by those skilled in the art that various changes may be made and equivalents may be substituted for elements thereof without departing from the scope of the present disclosure. In addition, many modifications may be made to adapt a particular situation or material to the teachings of the present disclosure without departing from the essential scope thereof. Therefore, it is intended that the present disclosure not be limited to the particular embodiment disclosed as the best mode contemplated for carrying out this present disclosure, but that the present disclosure will include all embodiments falling within the scope of the claims.

What is claimed is:

1. A refrigerant detection assembly operable to detect refrigerant mixed with air, the refrigerant detection assembly comprising:
    a housing having an internal cavity fluidly connected with an ambient atmosphere surrounding the housing via at least one opening; and
    a sensor subassembly mounted within the internal cavity, the sensor subassembly comprising:
        a sensor;
        a printed circuit board;
        a heat preservation housing mechanically and thermally coupled to the printed circuit board;
        a top shielding component mechanically coupled to the printed circuit board, the top shielding component being distinct from and positioned in overlapping arrangement with an upper surface of the heat preservation housing; and
        a bottom shielding component arranged at an opposite side of the printed circuit board as the top shielding component, the bottom shielding component being mechanically fastened to the top component, wherein the top shielding component and the bottom shielding component are positioned within the internal cavity of the housing.

2. The refrigerant detection assembly of claim 1, wherein the sensor is a non-dispersive infrared sensor.

3. The refrigerant detection assembly of claim 2, wherein the non-dispersive infrared sensor includes a light source and a detector element, the light source and the detector element being mounted to the printed circuit board.

4. The refrigerant detection assembly of claim 1, further comprising a bottom shielding component, the top shielding component being mechanically fastened to the bottom shielding component.

5. The refrigerant detection assembly of claim 4, wherein the bottom shielding component is positioned adjacent a bottom surface of the printed circuit board.

6. The refrigerant detection assembly of claim 1, wherein the sensor is encased between the heat preservation housing and the printed circuit board.

7. The refrigerant detection assembly of claim 6, wherein the heat preservation housing has at least one hole formed therein.

8. The refrigerant detection assembly of claim 1, wherein the subassembly further comprises at least one active heating element operably coupled to the non-dispersive infrared sensor.

9. The refrigerant detection assembly of claim 1, further comprising a film disposed in overlapping arrangement with the at least one opening, wherein the film is permeable to gas and impermeable to liquid.

10. A heating ventilation and air conditioning (HVAC) system comprising:
    a heat exchanger arranged within a closed loop refrigerant circuit; and
    a refrigerant detection assembly operable to detect refrigerant from the closed loop refrigerant circuit mixed with air, the refrigerant detection assembly comprising:
        a housing having an internal cavity and an opening such that a flow path extends from the opening into the internal cavity; and
        a sensor subassembly mounted within the internal cavity, the sensor subassembly comprising:
            a sensor;
            a printed circuit board;
            a heat preservation housing mechanically and thermally coupled to the printed circuit board; and
            a top shielding component mechanically coupled to the printed circuit board, the top shielding component being distinct from and positioned in overlapping arrangement with an upper surface of the heat preservation housing; and
            a bottom shielding component arranged at an opposite side of the printed circuit board as the top shielding component, the bottom shielding component being mechanically fastened to the top shielding component, wherein the top shielding component and the bottom shielding component are positioned within the internal cavity of the housing.

11. The HVAC system of claim 10, wherein the heat exchanger is an evaporator and the refrigerant detection assembly is mounted adjacent to the evaporator coil.

12. The HVAC system of claim 10, wherein the refrigerant detection assembly is operable to detect a leak within the closed loop refrigerant circuit within ten seconds of being exposed to 100% of a lower flammability limit.

13. The HVAC system of claim 10, wherein the refrigerant detection assembly detects a leak within the closed loop refrigerant circuit when the refrigerant measured by the non-dispersive infrared sensor is at least 25% of a lower flammability limit.

14. The HVAC system of claim 10, wherein the sensor is integrated with the printed circuit board.

15. The HVAC system of claim 10, wherein the sensor is a non-dispersive infrared sensor.

16. The HVAC system of claim 10, wherein the sensor subassembly further comprises at least one active heating element operably coupled to the sensor.

17. The HVAC system of claim 10, wherein the top shielding component is directly mechanically fastened to the bottom shielding component.

18. The HVAC system of claim 10, further comprising:
a film disposed in overlapping arrangement with the opening, the film being permeable to gas and impermeable to liquid.

* * * * *